United States Patent
Dinc

(10) Patent No.: US 11,357,885 B2
(45) Date of Patent: Jun. 14, 2022

(54) INTERNAL COMPRESSION TREATMENT (ICT)

(71) Applicant: RD GLOBAL ARASTIRMA GELISTIRME SAGLIK ILAC INSAAT YATIRIMLARI SANAYI VE TICARET ANONIM SIRKETI, Ankara (TR)

(72) Inventor: Rasit Dinc, Ankara (TR)

(73) Assignee: RD GLOBAL ARASTIRMA GELISTIRME SAGLIK ILAC INSAAT YATIRIMLARI SANAYI VE TICARET ANONIM SIRKETI, Ankara (TR)

( * ) Notice: Subject to any disclaimer, the term of this patent is extended or adjusted under 35 U.S.C. 154(b) by 219 days.

(21) Appl. No.: 16/633,173

(22) PCT Filed: Jul. 25, 2018

(86) PCT No.: PCT/TR2018/050398
§ 371 (c)(1),
(2) Date: Jan. 23, 2020

(87) PCT Pub. No.: WO2019/139551
PCT Pub. Date: Jul. 18, 2019

(65) Prior Publication Data
US 2021/0154353 A1   May 27, 2021

(30) Foreign Application Priority Data

Jul. 26, 2017   (TR) .................... 2017/10921

(51) Int. Cl.
| | |
|---|---|
| *A61L 24/04* | (2006.01) |
| *A61B 17/12* | (2006.01) |
| *A61M 25/01* | (2006.01) |

(52) U.S. Cl.
CPC ...... *A61L 24/043* (2013.01); *A61B 17/12195* (2013.01); *A61M 25/0108* (2013.01)

(58) Field of Classification Search
CPC ............ A61B 17/12; A61B 17/12195; A61B 2017/00783; A61B 2017/00893; A61B 2017/22041; A61L 24/043; A61L 25/0108; A61M 2039/062
See application file for complete search history.

(56) References Cited

U.S. PATENT DOCUMENTS

| | | | |
|---|---|---|---|
| 2005/0142163 A1* | 6/2005 | Hunter | A61P 1/00 424/423 |
| 2005/0149173 A1* | 7/2005 | Hunter | A61B 17/11 623/1.42 |
| 2010/0217313 A1* | 8/2010 | Raabe | A61B 17/1325 606/213 |
| 2012/0059308 A1* | 3/2012 | Hsu | A61N 1/0502 604/21 |

(Continued)

*Primary Examiner* — Jocelin C Tanner
(74) *Attorney, Agent, or Firm* — Bayramoglu Law Offices LLC

(57) ABSTRACT

A system related to the reparation of damaged veins along with the suspension of venous stasis progression by minimizing the leak reflux flow and the protection of the valve functions of the vena saphena magna, parva, perforator veins by means of exovascular or external filling agent injection in the treatment of venous stasis (which is also called varicose vein or varicose treatment).

6 Claims, 1 Drawing Sheet

(56) References Cited

U.S. PATENT DOCUMENTS

| | | | |
|---|---|---|---|
| 2013/0116633 A1* | 5/2013 | Lichty, II | A61B 17/00491 |
| | | | 604/264 |
| 2015/0190127 A1 | 7/2015 | Madsen et al. | |
| 2016/0213607 A1 | 7/2016 | Ragg | |

* cited by examiner

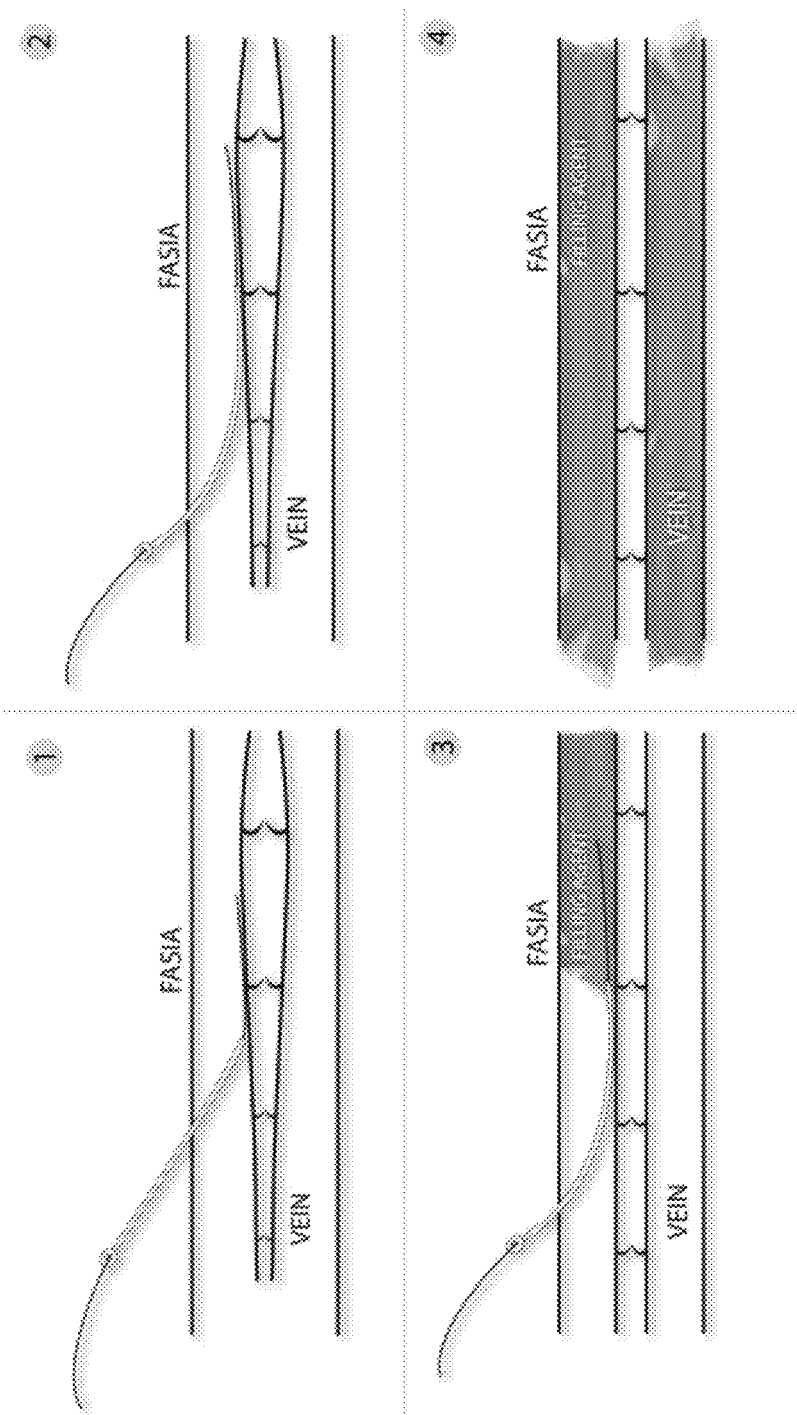

INTERNAL COMPRESSION TREATMENT (ICT)

CROSS REFERENCE TO THE RELATED APPLICATIONS

This application is the national phase entry of International Application No. PCT/TR2018/050398, filed on Jul. 25, 2018, which is based upon and claims priority to Turkish Patent Application No. 2017/10921, filed on Jul. 26, 2017, the entire contents of which are incorporated herein by reference.

TECHNICAL FIELD

The invention relates to an internal compression method of vena saphena magna, parva, perforator veins used in the treatment of venous stasis (varicose vein or varicose treatment).

BACKGROUND

Venous stasis is defined to be resulting from the leak and reflux originating from the expansion of vena saphena magna, vena saphena parva or perforator veins, which proceed in parallel to the deep vein (femoral vein). As an alternative to surgical methods, in the last 15 years, the related leaking veins are being closed by cauterization (intravenously, in an invasive manner) by means of endovenous interventions. Still, within the last few years, treatments such as thermal abrasion are carried out together with endovenous interventions with embolization agents.

The present technologies and treatments aim to close the vein intravenously by means of surgically removing the problematic vein segment, stripping or ligation of the same, or by means of thermal or embolization methods. All the present treatment methods are directed at providing treatment by eliminating and preventing the function of the problematic vein rather than repairing the same.

SUMMARY

The present varicose treatment methods in the world are carried out with the purpose of eliminating the varicose vein. The internal compression treatment (ICT) subject to the invention, which is a novel technique, is a medical device system which is designed for treating the varicose vein instead of eliminating it. It is a system related to the reparation of the damaged vein along with the suspension of the progress of venous stasis by minimizing the leak reflux flow and protection of the valve function by means of exovascular or external filling agent injection.

The invention is related to an innovative system which enables the protection of valve functions, suspension of the progress of outset varicosis and providing venous stasis treatment by means of a protective and reparative treatment through the application of a biocompatible filling agent such as biocompatible cyanoacrylate, hyaluronic acid, Botulinum toxin, sclerosant agent between 0-1000 Centipoises (cps) density (suggested density is 75-100 cps) exovascularly (extravascular) onto the problematic valve segments of the venous structures in which venous stasis is present, such as the saphenous vein, popliteal vein, perforator vein etc.

BRIEF DESCRIPTION OF THE DRAWINGS

FIG. 1: Application method of the filling agent

DETAILED DESCRIPTION

The invention is composed of 2 main elements. A biocompatible filling agent such as biocompatible cyanoacrylate (n-butyl, n-butyl-2, octyl, octyl-2 or octa-butyl cyanoacrylates), hyaluronic acid, ethylene vinyl alcohol copolymer DMSO, Botulinum toxin between 0-1000 cps density (suggested density is 75-100 cps) and an echogenic and rigid catheter custom-engineered for this procedure. For example, 1 unit of hyaluronic acid and 2 units of cyanoacrylate can be used in the filling agent.

A percutaneous entrance is made under ultrasonographic imaging with the help of a needle into the vein trace between the muscle fascia and the target vein planned to be treated. The trace is expanded by making a small amount of liquid injection with a liquid such as dextrose solution or physiological saline solution between the vein and the muscular layer named fascia. A rigid guide is pushed towards the target segment through the same needle. For this procedure, a catheter comprising stainless steel (SS) or nitinol coil reinforced PTFE hydrophilic coating is pushed into the procedure area through the guide wire by withdrawing the needle. A biocompatible filling agent such as biocompatible cyanoacrylate, hyaluronic acid, Botulinum toxin between 0-1000 cps) density suggested density is 75-100 cps) is injected exovascularly (extravascular) onto the problematic valve segments of the venous structures in which venous stasis is present, such as the saphenous vein, popliteal vein, perforator vein by means of the catheter under ultrasound until the leak reflux flow decreases between the range of 0.5-1 sec. In order to monitor the maximum vein diameter during injection, the patient needs to hold his/her breath and strain. The treatment is completed after making the necessary trace and valve checks at the end of the procedure. In this procedure, the treatment is applied not only to a single part of the vein segment, but to the entire problematic segment across the trace.

In a sample application, the fascia is opened by applying dextrose between the fascia and the vein by means of the catheter and the guide wire is pushed through this opening. Connective tissue enhancing drugs such as hyaluronic acid, gluconic acid can be used in order to reinforce the filling agent and repair the muscle. The filling agent should be injected with a pressure less than 10 mm hg pressure. It can be used in all venous system leaks. Vena saphena magna, parva, perforator vein leaks, deep venous insufficiency, primary deep venous insufficiency are examples. Indicators may be present on the application catheter.

What is claimed is:

1. An internal compression system, comprising an echogenic rigid catheter, a biocompatible filling agent having a density between 0-1000 Centipoises (cps), and hyaluronic acid as a connective tissue enhancer,
   wherein
   the biocompatible filling agent comprises a cyanoacrylate selected from the group consisting of n-butyl cyanoacrylate, butyl 2-cyanoacrylate, octyl cyanoacrylate, octyl 2-cyanoacrylate, and octa-butyl cyanoacrylate;
   wherein the internal compression system comprises 1 unit of hyaluronic acid and 2 or 3 units of the cyanoacrylate; and
   the internal compression system enables an exovascular injection onto problematic valve segments of a venous structure.

2. The internal compression system according to claim 1, wherein the echogenic rigid catheter is a catheter having a diameter of 4 F, 5 F, 6 F, 7 F, and 8 F and the echogenic rigid catheter contains PTFE, polyether block amides (pebax), PE, a metal, or is made of a metal.

3. The internal compression system according to claim 1, wherein the density of the biocompatible filling agent is 5-100 cps.

4. The internal compression system according to claim 1, wherein the biocompatible filling agent further comprises ethylene vinyl alcohol, Botulinum toxin, ethylene vinyl alcohol-co-polymer-DMSO or mixtures thereof.

5. The internal compression system according to claim 1, wherein the connective tissue enhancer further comprises gluconic acid.

6. The internal compression system according to claim 1, wherein the biocompatible filling agent further comprises ethylene vinyl alcohol, Botulinum toxin, ethylene vinyl alcohol-co-polymer-DMSO or mixtures thereof, and wherein the connective tissue enhancer further comprises gluconic acid.

* * * * *